United States Patent [19]
Nawamaki et al.

[11] Patent Number: 6,030,925
[45] Date of Patent: Feb. 29, 2000

[54] HERBICIDAL COMPOSITION

[75] Inventors: Tsutomu Nawamaki; Kimihiro Ishikawa, both of Shiraoka-machi, Japan

[73] Assignee: Nissan Chemical Industries, Ltd., Tokyo, Japan

[21] Appl. No.: 09/117,454

[22] PCT Filed: Jan. 24, 1997

[86] PCT No.: PCT/JP97/00158

§ 371 Date: Sep. 14, 1998

§ 102(e) Date: Sep. 14, 1998

[87] PCT Pub. No.: WO97/27753

PCT Pub. Date: Aug. 7, 1997

[30] Foreign Application Priority Data

Feb. 2, 1996 [JP] Japan .................................... 8-017788
Dec. 19, 1996 [JP] Japan .................................... 8-339428

[51] Int. Cl.[7] .......................... A01N 43/54; A01N 43/64
[52] U.S. Cl. ........................ 504/134; 504/133; 504/136
[58] Field of Search ................. 504/133, 134, 504/136

[56] References Cited

U.S. PATENT DOCUMENTS

| | | | |
|---|---|---|---|
| 4,370,480 | 1/1983 | Levitt et al. | 544/320 |
| 4,668,277 | 5/1987 | Yamamoto et al. | 71/92 |
| 4,954,164 | 9/1990 | Suzuki et al. | 71/92 |
| 5,474,971 | 12/1995 | Sandell | 504/116 |

FOREIGN PATENT DOCUMENTS

| | | |
|---|---|---|
| B 85572/91 | 4/1992 | Australia . |
| 2-160706 | 6/1990 | Japan . |
| 3-501479 | 4/1991 | Japan . |
| 5-229907 | 9/1993 | Japan . |
| 5-320011 | 12/1993 | Japan . |
| 7-300403 | 11/1995 | Japan . |
| 8-133912 | 5/1996 | Japan . |

OTHER PUBLICATIONS

Tomlin, "The Pesticide Manual Incorporating the Agrochemicals Handbook," 10th ed. (1995) pp. 549,550,701,702, 873 & 874.

*Primary Examiner*—Allen J. Robinson
*Attorney, Agent, or Firm*—Oblon, Spivak, McClelland, Maier & Neustadt, P.C.

[57] ABSTRACT

A herbicidal composition comprising metsulfuron methyl and at least one compound selected from the group consisting of pyrazosulfuron ethyl and halosulfuron methyl as active ingredients, and a method for controlling weeds comprising using the composition.

10 Claims, No Drawings

006,030,925

HERBICIDAL COMPOSITION

This application is a 371 of PCT/JP97/00158, filed Jan. 24, 1997.

FIELD OF THE INVENTION

The present invention relates to a herbicidal composition comprising at least two kinds of known herbicidally active ingredients, which can effectively control various harmful weeds in a paddy field.

BACKGROUND OF INVENTION

Various kinds of herbicides have been put to practical use by research and development concerning a herbicide for many years, which herbicides have contributed to laborsaving in controlling weeds and improving productivity of farm and garden crops. Development of a new herbicide having a more excellent herbicidal activity is, however, still needed. In particular, a herbicide for paddy rice is needed which can selectively control target weeds in lower dose without any phytotoxicity to paddy rice. Existing herbicides, however, do not necessarily meet these requirements.

Pyrazosulfuron ethyl (Common name; hereinafter referred to as Compound (I-1)), which can provide an excellent herbicidal effect with a lower dose as compared with conventional herbicides and show good safety to paddy rice, has been practically used. But pyrazosulfuron ethyl has inadequate effects on some weeds.

Halosulfuron methyl (Common name; hereinafter referred to as Compound (I-2)), which can provide an excellent herbicidal effect with a lower dose as compared with conventional herbicides and show good safety to corn, has been practically used for corn and suggested to apply to paddy rice. But halosulfuron methyl has inadequate effects on some weeds.

Metsulfuron methyl (Common name; hereinafter referred to as Compound (II)), which can also provide an excellent herbicidal effect with a lower dose as compared with conventional herbicides, has been practically used as a herbicide for wheat. Metsulfuron methyl is, however, less effective to Cyperaceae weeds and sometimes cause phytotoxicity to paddy rice with a higher dose, while it shows safety to paddy rice with a lower dose.

SUMMARY OF THE INVENTION

This invention relates to a herbicidal composition comprising Compound (II) and at least one compound selected from the group consisting of Compound (I-1) and Compound (I-2) as active ingredients (hereinafter referred to as the composition of the present invention).

According to the composition of the present invention, Compound (I-1), Compound (I-2) and Compound (II) can provide their herbicidal effects synergistically more than additively, and consequently the amount of each compound to be applied can be reduced.

The composition of the present invention is practically quite useful, since it can completely control many weeds with a low dose without any phytotoxicity to paddy rice. The composition of the present invention is highly effective to weeds in both pre-emergence soil treatment and post-emergence foliar treatment.

DETAILED DESCRIPTION OF THE INVENTION

In the composition of the present invention, Compound (II) is blended with Compound (I-1) and Compound (I-2) preferably at the ratio of 0.001–10 parts by weight of Compound (II) per 1 part by weight of Compound (I-1) and Compound (I-2), more preferably 0.01–1 parts by weight of Compound (II) per 1 part by weight of Compound (I-1) and Compound (I-2).

Suitable application rate of the composition of the present invention will vary depending on a type of target weed and the like. In general, the application rate is set such that it preferably corresponds to 1 g–1 kg/ha of Compound (I-1) or Compound (I-2) and 0.1–100 g/ha of Compound (II) as active ingredients, more preferably 5–100 g/ha of the former and 1–50 g/ha of the latter.

The composition of the present invention is usually used in a form of a formulation in which the active ingredients are mixed with a carrier usually consisting of a solid or liquid diluent. The formulation preferably also contains a surfactant.

Such an applicable carrier includes a solid carrier such as clay, talc, bentonite, diatomaceous earth and white carbon; and a liquid carrier such as water, alcohols (isopropanol, butanol, benzyl alcohol, furfuryl alcohol, etc.), aromatic hydrocarbons (toluene, xylene, etc.), chlorinated hydrocarbons (chlorobenzene, etc.), ethers (anisol, etc.), ketones (cyclohexanone, isophorone, etc.), esters (butyl acetate, etc.), acid amides (N-methyl pyrrolidone, etc.).

Such an applicable surfactant includes an anionic surfactant such as sodium alkylarylsulfonates, sodium alkylnaphthalenesulfonates, sodium dialkylsuccinates, polyoxyethylene alkylaryl ether sulfates, alkyl type of phosphates and alkylphenol type of phosphates; a nonionic surfactant such as polyoxyethylene alkyl ethers, polyoxyethylene alkylaryl ethers, polyoxyethylene (propylene) fatty acid esters, sorbitan monooleate and polyoxyethylenesorbitan monolaurate; and a vegetable oil derivative such as polyoxyethylene hardened castor oil.

The composition of the present invention, if necessary, can also be added with an emulsifier, wetting agent, dispersant, binder, penetrating agent, spreader and/or stabilizer, and can be practically used in a desirable formulation such as an emulsifiable concentrate, liquid formulation, wettable powder, dust formulation, granule, granular wettable powder or flowable.

The composition of the present invention can be used in combination with one or more known herbicides. Preferable herbicides which are used in combination with the composition of the present invention include bensulfuron methyl (Common name), cinosulfuron (Common name), imazosulfuron (Common name), pretilachlor (Common name), esprocarb (Common name), pyrazolate (Common name), pyrazoxyfen (Common name), benzofenap (Common name), bromobutide (Common name), naproanilide (Common name), clomeprop (Common name), CNP (Common name), chlomethoxynil (Common name), bifenox (Common name), oxadiazon (Common name), mefenacet (Common name), butachlor (Common name), butenachlor (Common name), dithiopyr (Common name), benfuresate (Common name), pyributicarb (Common name), benthiocarb (Common name), dimepiperate (Common name), molinate (Common name), butamifos (Common name), quinclorac (Common name), cinmethylin (Common name), propanil (Common name), simetryn (Common name), bensulide (Common name), dimethametryn (Common name), methyldymron (Common name), anilofos (Common name), MCPA, MCPB, cafenstrole (Common name), thenylchlor (Common name), 2',3'-dichloro-ethoxymethoxybenzanilide (test name: HW-52), 1-(2-chlorobenzyl)-3-(α, α-dimethylbenzyl)urea (test name: JC-940), N-(2-fluoro-4-chloro-5-cyclopentyloxyphenyl)-5-isopropylidene-1,3-oxazolidine-2,4-dione (test name: KPP-314), n-butyl-(R)-2-[4-(2-fluoro-4-cyanophenoxy)phenoxy]propionate (test name: DEH-112), methyl 2-[(4,6-dimethoxypyrimidin-2-yl)oxy]-6-[1-(methoxyimino)ethyl]benzoate (test name: KUH-920), 2-[2-(3-chlorophenyl)-2,3-epoxypropyl]-2-ethylindane-1,3-dione (test name: MK-243), bentazone (Common name), dymron (Common name) and compounds listed in WO-9321162 and JP-A-6-184115.

The composition of the present invention can be used as a herbicidal composition for paddy field in both foliar treatment and soil treatment under flooded condition. Paddy weeds include Alismataceae weeds represented by *Alisma canaliculatum, Sagittaria trifolia, Sagittaria pygmaea* and the like; Cyperaceae weeds represented by *Cyperus difformis, Cyperus serotinus, Scirpus juncoides, Eleocharis kuroauwai* and the like; Scrothulariaceae weeds represented by *Lindernia pyxidaria* and the like; Potenderiaceae weeds represented by *Monochoria vaginalis* and the like; Potamogetonaceae weeds represented by *Potamogeton distinctus* and the like; Lythraceae weeds represented by *Rotala indica* and the like; and Gramineae weeds represented by *Echinochloa crus-galli* and the like.

A synergistic herbicidal effect of a herbicide mixture can be explained as follows. Two herbicidally active compounds, each of which often has defects in its herbicidal activity, may be combined each other to provide a higher activity than an expected activity which is an activity obtained by simply adding each activity of them. Such a higher activity is called a synergistic effect. An expected activity from a specific combination of two herbicides can be estimated as follows (See Colby S. R., "Estimation of a synergistic and antagonistic effect of combined herbicides", *Weed,* Vol. 15, pp. 20–22 (1967).).

$$E = \alpha + \beta - (\alpha \times \beta / 100)$$

α: a control rate achieved by Herbicide A when it is applied in the application rate of "a" kg/ha;
β: a control rate achieved by Herbicide B when it is applied in the application rate of "b" kg/ha;
E: an expected control rate when Herbicide A and B are applied in the application rates of "a" kg/ha and "b" kg/ha, respectively.

Thus, when a control rate actually achieved is higher than the expected control rate obtained by the above calculation, it can be concluded that the effect provided by the combination is a synergistic effect.

EXAMPLES

The following Examples illustrate the composition of the present invention. The compounds, production amounts, formulations according to the present invention, however, should not be limited to the Examples. In the following description, "part(s)" signifies part(s) by weight.

| [Wettable powder] | parts |
|---|---|
| The composition of the present invention | 0.1–80 |
| Solid carrier | 10–90 |
| Surfactant | 1–10 |
| Others | 1–5 |

(Others, for example, include a coagulation preventing agent and the like.)

| | parts |
|---|---|
| [Emulsifiable Concentrate] | |
| The composition of the present invention | 0.1–30 |
| Liquid carrier | 55–95 |
| Surfactant | 4.9–15 |
| [Flowable] | |
| The composition of the present invention | 0.1–70 |
| Liquid carrier | 15–65 |
| Surfactant | 5–12 |
| Others | 5–30 |

(Others, for example, include an anti-freezing agent and a thickener and the like.)

| | parts |
|---|---|
| [Granular Wettable Powder] (Dry Flowable) | |
| The composition of the present invention | 0.1–90 |
| Solid carrier | 5–70 |
| Surfactant | 1–30 |
| [Liquid Formulation] | |
| The composition of the present invention | 0.01–30 |
| Liquid carrier | 0.1–50 |
| Water | 50–99.99 |
| Others | 0.1–10 |
| [Granule] | |
| The composition of the present invention | 0.01–10 |
| Solid carrier | 90–99.99 |
| Others | 0–10 |

| Formulation Example 1: Granule | parts |
|---|---|
| Compound (I-1) | 5 |
| Compound (II) | 1 |
| Bentonite | 55 |
| Talc | 39 |

The above ingredients are homogeneously blended and ground, to which then a small amount of water is added, and the resulting mixture is kneaded with stirring, granulated by an extrusion granulator and dried to formulate a granule.

| Formulation Example 2: Granular Wettable Powder (Dry Flowable) | parts |
|---|---|
| Compound (I-1) | 60 |
| Compound (II) | 10 |
| Isobam No. 1 (trademark) | 15 |
| (anionic surfactant: Kuraray Isoprene Chemical Co., Ltd.) | |
| Vanilex N (trademark) | 5 |
| (anionic surfactant: Sanyo Kokusaku Pulp K.K.) | |
| Carplex #80 (trademark) | 10 |
| (white carbon: Shionogi Pharmaceutical Co., Ltd.) | |

The above ingredients are homogeneously blended and finely ground to formulate a dry flowable.

| Formulation Example 3: Wettable powder | parts |
|---|---|
| Compound (I-1) | 40 |
| Compound (II) | 8 |
| Zeeklite PFP (trademark) | 45 |
| (kaolin type clay: Zeeklite Industries Co., Ltd.) | |
| Sorpol 5050 (trademark) | 2 |
| (anionic surfactant: Toho Chemical Co., Ltd.) | |
| Runox 1000 C (trademark) | 3 |
| (anionic surfactant: Toho Chemical Co., Ltd.) | |
| Carplex #80 (trademark) | 2 |
| (coagulation preventing agent) | |
| (white carbon: Shionogi Pharmaceutical Co., Ltd.,) | |

The above ingredients are homogeneously blended and ground to formulate a wettable powder.

| Formulation Example 4: Granule | parts |
|---|---|
| Compound (I-2) | 5 |
| Compound (II) | 1 |
| Bentonite | 55 |
| Talc | 39 |

The above ingredients are homogeneously blended and ground, to which then a small amount of water is added, and the resulting mixture is kneaded with stirring, granulated by an extrusion granulator and dried to formulate a granule.

| Formulation Example 5: Granular Wettable Powder (Dry Flowable) | parts |
|---|---|
| Compound (I-2) | 60 |
| Compound (II) | 10 |
| Isobam No. 1 (trademark) | 15 |
| (anionic surfactant: Kuraray Isoprene Chemical Co., Ltd.) | |
| Vanilex N (trademark) | 5 |
| (anionic surfactant: Sanyo Kokusaku Pulp K.K.) | |
| Carplex #80 (trademark) | 10 |
| (white carbon: Shionogi Pharmaceutical Co., Ltd.) | |

The above ingredients are homogeneously blended and finely ground to formulate a dry flowable.

| Formulation Example 6: Wettable powder | parts |
|---|---|
| Compound (I-2) | 40 |
| Compound (II) | 8 |
| Zeeklite PFP (trademark) | 45 |
| (kaolin type clay: Zeeklite Industries Co., Ltd.) | |
| Sorpol 5050 (trademark) | 2 |
| (anionic surfactant: Toho Chemical Co., Ltd.) | |
| Runox 1000 C (trademark) | 3 |
| (anionic surfactant: Toho Chemical Co., Ltd.) | |
| Carplex #80 (trademark) | 2 |
| (coagulation preventing agent) | |
| (white carbon: Shionogi Pharmaceutical Co., Ltd.) | |

The above ingredients are homogeneously blended and ground to formulate a wettable powder.

The following Test Examples specifically show that the composition of the present invention is useful as a herbicide.

Test Example 1: Test on Herbicidal Effect by Pre-emergence Treatment Under Flooded Condition An alluvial soil was placed in 1/5000 are Wagner pots and then water was poured thereinto to puddle the soil to prepare a flooded condition with 4 cm of the depth of water. After seeds of *Monochoria vaginalis* and *Scirpus juncoides* are sown and tubers of *Sagittaria pygmaea* and *Cyperus serotinus* are placed on the soil, 2.5-leaf stage rice seedlings were transplanted. On the day of transplanting the rice seedlings, a predetermined concentration of suspension of each test compound, which was prepared using a wettable powder formulated by way of experiment in accordance with the above formulation example, was dropped onto the water surface with a measuring pipette. Three weeks after the application of each compound, fresh weights of aerial parts of each weed and rice plant were weighed to determine a control rate (%) using the following equation.

A control rate (%)=[1-(fresh weight of aerial parts of the treated weeds and rice plants)/(fresh weight of aerial parts of the untreated weeds and rice plants)]×100

The results obtained are shown in Table 1 and Table 2.

In these tables, symbols represent the following meanings;

A: *Monochoria vaginalis*, B: *Scirpus juncoides*, C: *Sagittaria pygmaea*, D: *Cyperus serotinus*, R: transplanted rice.

TABLE 1

Herbicidal effects of single formulations (control rates (%))

| Compound | Application Rate (g a.i./ha) | A | B | C | D | R |
|---|---|---|---|---|---|---|
| Compound (I-1) | 3 | 46 | 72 | 67 | 55 | 0 |
|  | 4 | 65 | 80 | 71 | 60 | 0 |
|  | 6 | 72 | 85 | 82 | 75 | 0 |
|  | 9 | 87 | 94 | 95 | 90 | 0 |
|  | 10 | 93 | 98 | 98 | 95 | 0 |
|  | 12 | 98 | 99 | 99 | 98 | 0 |
| Compound (II) | 1 | 65 | 47 | 23 | 5 | 0 |
|  | 3 | 88 | 87 | 75 | 20 | 0 |
|  | 4 | 92 | 95 | 80 | 31 | 5 |
|  | 6 | 98 | 99 | 92 | 42 | 28 |

TABLE 2

Herbicidal effects of the composition of the present invention;
actually found values (F) and expected values (E) (control rates (%))

| Compound | Application Rate (gai/ha) | Plant A (F) | (E) | B (F) | (E) | C (F) | (E) | D (F) | (E) | R (F) | (E) |
|---|---|---|---|---|---|---|---|---|---|---|---|
| Compound (I-1) + (II) | 3 + 1 | 100 | 81 | 100 | 85 | 100 | 75 | 86 | 57 | 0 | 0 |
|  | 3 + 3 | 100 | 95 | 100 | 97 | 100 | 96 | 100 | 64 | 0 | 0 |
|  | 9 + 1 | 100 | 94 | 100 | 96 | 100 | 92 | 96 | 91 | 0 | 0 |
|  | 9 + 3 | 100 | 98 | 100 | 99 | 100 | 99 | 100 | 92 | 0 | 0 |

(In the table, the expected values are those calculated with the above Colby's equation. In the application rate of active ingredient of the mixture composition, a left value is the application rate of Compound (I-1) and a right value is the application rate of Compound (II).)

TABLE 3

Herbicidal effects of single formulations (control rates (%))

| Compound | Application Rate (g a.i./ha) | A | B | C | D | R |
|---|---|---|---|---|---|---|
| Compound (I-2) | 3 | 39 | 65 | 60 | 43 | 0 |
|  | 4 | 64 | 75 | 70 | 55 | 0 |
|  | 6 | 70 | 84 | 78 | 71 | 0 |
|  | 9 | 85 | 90 | 95 | 86 | 0 |
|  | 10 | 95 | 97 | 96 | 96 | 0 |
|  | 12 | 98 | 99 | 99 | 98 | 0 |

TABLE 4

Herbicidal effects of the composition of the present invention;
actually found values (F) and expected values (E) (control rates (%))

| Compound | Application Rate (gai/ha) | Plant A (F) | (E) | B (F) | (E) | C (F) | (E) | D (F) | (E) | R (F) | (E) |
|---|---|---|---|---|---|---|---|---|---|---|---|
| Compound (I-2) + (II) | 3 + 1 | 100 | 79 | 100 | 81 | 100 | 69 | 83 | 46 | 0 | 0 |
|  | 3 + 3 | 100 | 93 | 100 | 95 | 100 | 90 | 90 | 57 | 0 | 0 |
|  | 9 + 1 | 100 | 95 | 100 | 95 | 100 | 96 | 100 | 87 | 0 | 0 |
|  | 9 + 3 | 100 | 98 | 100 | 99 | 100 | 99 | 100 | 89 | 0 | 0 |

(In the table, the expected values are those calculated with the above Colby's equation. In the application rate of active ingredient of the mixture composition, a left value is the application rate of Compound (I-2) and a right value is the application rate of Compound (II).)

Test Example 2: Test on Herbicidal Effect by Growing Stage Treatment Under Flooded Condition An alluvial soil was placed in 1/5000 are Wagner pots and then water was poured thereinto to puddle the soil to prepare a flooded condition with 4 cm of the depth of water. Seeds of barnyardgrass (*Echinochloa crus-galli*) and rice are sown. When the barnyardgrass grew to 2.5-leaf stage, a diluted solution of test compound was dropped onto the water surface with a measuring pipette so that predetermined amount of the compound was applied. Three weeks after treatment with the compound, herbicidal effects on the barnyardgrass and rice were evaluated according to the following criteria. The results obtained are shown in Table 5.

Evaluation Criteria

5: Completely killed or control rate is at least 90%;

4: Control rate is at least 70% to less than 90%;

3: Control rate is at least 40% to less than 70%;

2: Control rate is at least 20% to less than 40%;

1: Control rate is at least 5% to less than 20%;

0: Control rate is less than 5%.

The control rate was determined on the basis of visual observation.

TABLE 5

| Compound | Application Rate (g a.i./ha) | Plant Barnyardgrass | Rice |
|---|---|---|---|
| Compound (I-1) | 3 | 2 | 0 |
|  | 9 | 3 | 0 |
| Compound (I-2) | 3 | 2 | 0 |
|  | 9 | 3 | 0 |
| Compound (II) | 3 | 0 | 0 |
|  | 9 | 1 | 1 |
| Compound (I-1) + (II) | 3 + 1 | 4 | 0 |
|  | 3 + 3 | 5 | 0 |
|  | 9 + 1 | 5 | 0 |
|  | 9 + 3 | 5 | 0 |
| Compound | 3 + 1 | 4 | 0 |

TABLE 5-continued

| Compound | Application Rate (g a.i./ha) | Plant Barnyardgrass | Rice |
|---|---|---|---|
| (I-2) + (II) | 3 + 3 | 5 | 0 |
| | 9 + 1 | 5 | 0 |
| | 9 + 3 | 5 | 0 |

As apparent from the above results, the composition of the present invention provides much higher effects, which is synergistic effects, than additive effects expected from Compound (I-1), Compound (I-2) and Compound (II). The composition of the present invention can selectively control target weeds with a lower dose as compared with conventional herbicidal compositions.

We claim:

1. A herbicidal composition comprising (1) metsulfuron methyl and (2) at least one compound selected from the group consisting of pyrazosulfuron ethyl and halosulfuron methyl, as active ingredients, wherein components (1) and (2) are present in synergistic herbicidally effective amounts.

2. A method for controlling weeds in a locus of paddy rice comprising applying to said locus a synergistic herbicidally effective amount of the composition according to claim 1.

3. The herbicidal composition of claim 1, comprising pyrazosulfuron ethyl and metsulfuron methyl as active ingredients.

4. A method for controlling weeds in a locus of paddy rice comprising applying to said locus a synergistic herbicidally effective amount of the composition according to claim 3.

5. The herbicidal composition of claim 1, comprising halosulfuron methyl and metsulfuron methyl as active ingredients.

6. A method for controlling weeds in a locus of paddy rice comprising applying to said locus a synergistic herbicidally effective amount of the composition according to claim 5.

7. The method of claim 2, wherein said applying is a pre-emergence treatment under flooded conditions.

8. The method of claim 7, wherein the weed is at least one selected from the group consisting of *Monochoria vaginalis, Scirpus juncoides, Sagittaria pygmaea,* and *Cyperus serotinus.*

9. The method of claim 2, wherein said applying is a growing stage treatment under flooded condition.

10. The method of claim 9, wherein the weed is barnyard grass.

* * * * *